(12) United States Patent
Hashimoto et al.

(10) Patent No.: US 10,631,942 B2
(45) Date of Patent: Apr. 28, 2020

(54) REMOTE CONTROL ROBOT SYSTEM

(71) Applicant: KAWASAKI JUKOGYO KABUSHIKI KAISHA, Kobe-shi, Hyogo (JP)

(72) Inventors: Yasuhiko Hashimoto, Kobe (JP); Masayuki Kamon, Akashi (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 292 days.

(21) Appl. No.: 15/755,449

(22) PCT Filed: May 27, 2016

(86) PCT No.: PCT/JP2016/002597
§ 371 (c)(1),
(2) Date: Feb. 26, 2018

(87) PCT Pub. No.: WO2017/033367
PCT Pub. Date: Mar. 2, 2017

(65) Prior Publication Data
US 2018/0250829 A1 Sep. 6, 2018

(30) Foreign Application Priority Data
Aug. 25, 2015 (JP) .................... 2015-165479

(51) Int. Cl.
*G06F 19/00* (2018.01)
*A61B 34/37* (2016.01)
(Continued)

(52) U.S. Cl.
CPC .............. *A61B 34/37* (2016.02); *A61B 34/32* (2016.02); *B23P 19/04* (2013.01); *B23Q 15/12* (2013.01);
(Continued)

(58) Field of Classification Search
CPC .... A61B 34/37; A61B 34/32; G05B 19/4182; G06T 7/62; G06T 7/70; B25J 9/0081;
(Continued)

(56) References Cited

U.S. PATENT DOCUMENTS 6,590,633 B1 * 7/2003 Nishi ................. G03F 7/70358
269/21
2004/0133312 A1 7/2004 Watanabe et al.
(Continued)

FOREIGN PATENT DOCUMENTS

EP 0145683 A1 6/1985
JP S61-61191 U 4/1986
(Continued)

OTHER PUBLICATIONS

Aug. 9, 2016 International Search Report issued in International Patent Application No. PCT/JP2016/002597.
(Continued)

*Primary Examiner* — Ian Jen
(74) *Attorney, Agent, or Firm* — Oliff PLC (57) ABSTRACT

A robot main body having a robotic arm, a remote control device which includes a robotic arm operational instruction input part installed outside of a working area and by which an operational instruction for the robotic arm is inputted, and a contactless action detecting part configured to detect a contactless action including at least one given operating condition parameter change instructing action by an operator, a control device communicably connected to the remote control device and configured to control operation of the robot main body.

5 Claims, 6 Drawing Sheets

(51) Int. Cl.
| | |
|---|---|
| G05B 19/418 | (2006.01) |
| B23P 19/04 | (2006.01) |
| B25J 13/00 | (2006.01) |
| B25J 19/04 | (2006.01) |
| B25J 9/00 | (2006.01) |
| B25J 9/16 | (2006.01) |
| B25J 13/08 | (2006.01) |
| B25J 3/00 | (2006.01) |
| B25J 13/06 | (2006.01) |
| B25J 18/00 | (2006.01) |
| B25J 19/02 | (2006.01) |
| B25J 3/04 | (2006.01) |
| B23Q 15/12 | (2006.01) |
| B25J 13/02 | (2006.01) |
| B25J 11/00 | (2006.01) |
| G06F 3/01 | (2006.01) |
| H04N 5/232 | (2006.01) |
| H04N 7/18 | (2006.01) |
| A61B 34/32 | (2016.01) |
| G06T 7/62 | (2017.01) |
| G06T 7/70 | (2017.01) |
| B23P 21/00 | (2006.01) |

(52) U.S. Cl.
CPC . *B25J 3/00* (2013.01); *B25J 3/04* (2013.01); *B25J 9/0081* (2013.01); *B25J 9/0084* (2013.01); *B25J 9/0087* (2013.01); *B25J 9/161* (2013.01); *B25J 9/1602* (2013.01); *B25J 9/163* (2013.01); *B25J 9/1612* (2013.01); *B25J 9/1628* (2013.01); *B25J 9/1633* (2013.01); *B25J 9/1646* (2013.01); *B25J 9/1653* (2013.01); *B25J 9/1664* (2013.01); *B25J 9/1669* (2013.01); *B25J 9/1674* (2013.01); *B25J 9/1682* (2013.01); *B25J 9/1689* (2013.01); *B25J 9/1697* (2013.01); *B25J 11/008* (2013.01); *B25J 13/00* (2013.01); *B25J 13/003* (2013.01); *B25J 13/006* (2013.01); *B25J 13/02* (2013.01); *B25J 13/025* (2013.01); *B25J 13/06* (2013.01); *B25J 13/065* (2013.01); *B25J 13/08* (2013.01); *B25J 13/084* (2013.01); *B25J 13/085* (2013.01); *B25J 13/087* (2013.01); *B25J 13/088* (2013.01); *B25J 18/00* (2013.01); *B25J 19/023* (2013.01); *B25J 19/028* (2013.01); *B25J 19/04* (2013.01); *G05B 19/4182* (2013.01); *G06F 3/017* (2013.01); *G06T 7/62* (2017.01); *G06T 7/70* (2017.01); *H04N 5/23219* (2013.01); *H04N 7/181* (2013.01); *B23P 21/00* (2013.01); *B23P 21/002* (2013.01); *G05B 2219/33007* (2013.01); *G05B 2219/35464* (2013.01); *G05B 2219/37297* (2013.01); *G05B 2219/39004* (2013.01); *G05B 2219/39102* (2013.01); *G05B 2219/39439* (2013.01); *G05B 2219/39531* (2013.01); *G05B 2219/39533* (2013.01); *G05B 2219/40022* (2013.01); *G05B 2219/40134* (2013.01); *G05B 2219/40136* (2013.01); *G05B 2219/40139* (2013.01); *G05B 2219/40142* (2013.01); *G05B 2219/40143* (2013.01); *G05B 2219/40145* (2013.01); *G05B 2219/40146* (2013.01); *G05B 2219/40161* (2013.01); *G05B 2219/40162* (2013.01); *G05B 2219/40163* (2013.01); *G05B 2219/40169* (2013.01); *G05B 2219/40182* (2013.01); *G05B 2219/40183* (2013.01); *G05B 2219/40195* (2013.01); *G05B 2219/40387* (2013.01); *G05B 2219/40627* (2013.01); *Y10S 901/02* (2013.01); *Y10S 901/03* (2013.01); *Y10S 901/08* (2013.01); *Y10S 901/09* (2013.01); *Y10S 901/10* (2013.01); *Y10S 901/27* (2013.01); *Y10S 901/41* (2013.01); *Y10S 901/46* (2013.01); *Y10S 901/47* (2013.01)

(58) Field of Classification Search
CPC ...... B25J 9/1646; B25J 9/1653; B25J 9/1674; B25J 9/1612; B25J 19/028; B25J 9/1602; B25J 13/085; B25J 13/087; B25J 9/0084; B25J 9/1697; B25J 13/006; B25J 13/08; B25J 9/0087; B25J 3/00; B25J 9/1669; B25J 13/06; B25J 13/88; B25J 18/00; B25J 9/161; B25J 9/1664; B25J 9/1682; B25J 9/1689; B25J 19/023
See application file for complete search history.

(56) References Cited

U.S. PATENT DOCUMENTS

| | | | |
|---|---|---|---|
| 2008/0091244 A1* | 4/2008 | Richardson | A61B 5/053 607/9 |
| 2008/0275349 A1* | 11/2008 | Halperin | A61B 5/0205 600/484 |
| 2011/0118877 A1 | 5/2011 | Hwang et al. | |
| 2015/0127155 A1* | 5/2015 | Passot | B25J 9/163 700/257 |
| 2016/0303738 A1* | 10/2016 | Laurent | B25J 9/163 |
| 2017/0242714 A1* | 8/2017 | Chen | G06F 9/455 |
| 2017/0282371 A1* | 10/2017 | Erhart | B25J 9/1679 |
| 2017/0282375 A1* | 10/2017 | Erhart | B25J 11/0015 |

FOREIGN PATENT DOCUMENTS

| | | |
|---|---|---|
| JP | H09-216183 A | 8/1997 |
| JP | 2003-311661 A | 11/2003 |
| JP | 2014-104527 A | 6/2014 |
| TW | I301940 B | 10/2008 |
| TW | 200919210 A | 5/2009 |

OTHER PUBLICATIONS

May 15, 2017 Office Action issued in Taiwanese Patent Application No. 105127049.

* cited by examiner

|  | 1ST HAND GESTURE | 2ND HAND GESTURE |
|---|---|---|
| ATTITUDE OF RESPECTIVE FINGERS, HAND MOTION | | |
| INSTRUCTION CONTENT | ARM OPERATION SPEED INCREASE | ARM OPERATION SPEED REDUCTION |

FIG. 4

|  | 1ST SOUND | 2ND SOUND |
|---|---|---|
| SOUND CONTENT | "ARM SPEED UP" | "ARM SPEED DOWN" |
| INSTRUCTION CONTENT | ARM OPERATION SPEED INCREASE | ARM OPERATION SPEED REDUCTION |

REMOTE CONTROL ROBOT SYSTEM

TECHNICAL FIELD

The present disclosure relates to a remote control robot system.

BACKGROUND ART

Conventionally, systems including a remote operation control device which causes a robot to perform a necessary work are known (e.g., see Patent Document 1).

The remote operation control device of this system is the remote operation control device which causes the robot to perform the necessary operation while remotely controlling, by an operation control system, operation of the robot which is installed in a work environment. The remote operation control device includes an operational instruction generating means for generating an operational instruction for automatic operation of the robot, and a manipulating means for manually manipulating the robot. The robot is switched from the automatic operation to the manual manipulation in response to a switch instruction to the manual manipulation. Thus, against a work which is difficult to be automated, the work can be performed by being switched to the manual manipulation.

REFERENCE DOCUMENT OF CONVENTIONAL ART

Patent Document

[Patent Document 1] JP2003-311661A

DESCRIPTION OF THE DISCLOSURE

Problems to be Solved by the Disclosure

Meanwhile, when attempting to perform an input of a change instruction of an operating condition parameter related to an operating condition of a robot main body in addition to an input of an operational instruction of the robot, there has been a problem that, in addition to an input part by which the operational instruction of the robot is inputted, a means for inputting the change instruction of the operating condition parameter is required, resulted in a manipulating means having a complex structure. Further, with the configuration of the manipulating means being complex, there has been a problem that a required education period for an operator to be familiar with the method of controlling the manipulating means becomes longer.

SUMMARY OF THE DISCLOSURE

In order to solve the above problems, a remote control robot system according to one aspect of the present disclosure includes a robot main body having a robotic arm, a remote control device including a robotic arm operational instruction input part by which an operational instruction for the robotic arm is inputted, and a contactless action detecting part configured to detect a contactless action including at least one given operating condition parameter change instructing action by an operator, and a control device communicably connected to the remote control device and configured to control operation of the robot main body. The control device includes a memory part configured to store change instruction content data defining a change mode of an operating condition parameter related to an operating condition of the robot main body corresponding to the at least one operating condition parameter change instructing action, a change instruction content identifying module configured to identify the change mode of the operating condition parameter corresponding to one of the operating condition parameter change instructing action detected by the contactless action detecting part based on the change instruction content data, and a motion controlling module configured to control operation of the robot main body by changing the operating condition of the robot main body based on the change mode of the operating condition parameter identified by the change instruction content identifying module.

With this configuration, an action matching an impression on the operating condition parameter change instruction can be set as the operating condition parameter change instructing action, and a required education period for the operator to be familiar with the method of manipulating the remote control robot system can be shortened.

Further, since it is possible to input the operating condition parameter change instruction without touching, there is no need to visually recognize the contactless action detecting part at the time of inputting the operating condition parameter change instruction to the contactless action detecting part, and it is possible to promptly input the operating condition parameter change instruction to the contactless action detecting part.

Furthermore, it is possible that actions which are clearly distinguishable from each other as the respective operating condition parameter change instructing actions are selected and set as the operating condition parameter change instructing actions, preventing incorrect input and erroneous recognition by the operator.

The at least one operating condition parameter change instructing action may include a first action including a change from a first mode to a second mode, and a second action including a change from the second mode to the first mode. The change instruction content data may include a definition of the operating condition parameter change mode corresponding to the first action by which a value of the given operating condition parameter is increased, and a definition of the operating condition parameter change mode corresponding to the second action by which the value of the given operating condition parameter is reduced.

With this configuration, the operator can suitably input the increase/reduction instruction for the value of the operating condition parameter to the remote control robot system.

The operating condition parameter change instructing action may be an operator's hand gesture.

With this configuration, the operator can input the operating condition parameter change instruction by his/her hand gesture.

The hand gesture may be inputted by one of operator's hands.

With this configuration, it is possible to make a hand gesture with one hand to input the operational instruction for the robot main body to the remote control robot system, while simultaneously inputting another instruction to the remote control robot system with the other hand.

The operating condition parameter change instructing action may be operator's sound of voice.

With this configuration, the operating condition parameter change instruction can be inputted to the remote control robot system by the operator's sound of voice.

Effect of the Disclosure

The present disclosure exerts an effect that the required education period for the operator to be familiar with the method of manipulating the remote control robot system can be shortened.

MODES FOR CARRYING OUT THE DISCLOSURE

Hereinafter, embodiments of the present disclosure will be described with reference to the drawings. Note that the present disclosure is not to be limited by these embodiments. Further, below, the same reference characters are assigned to the same or corresponding components throughout the drawings and redundant description is omitted.

First Embodiment

Figure 1:
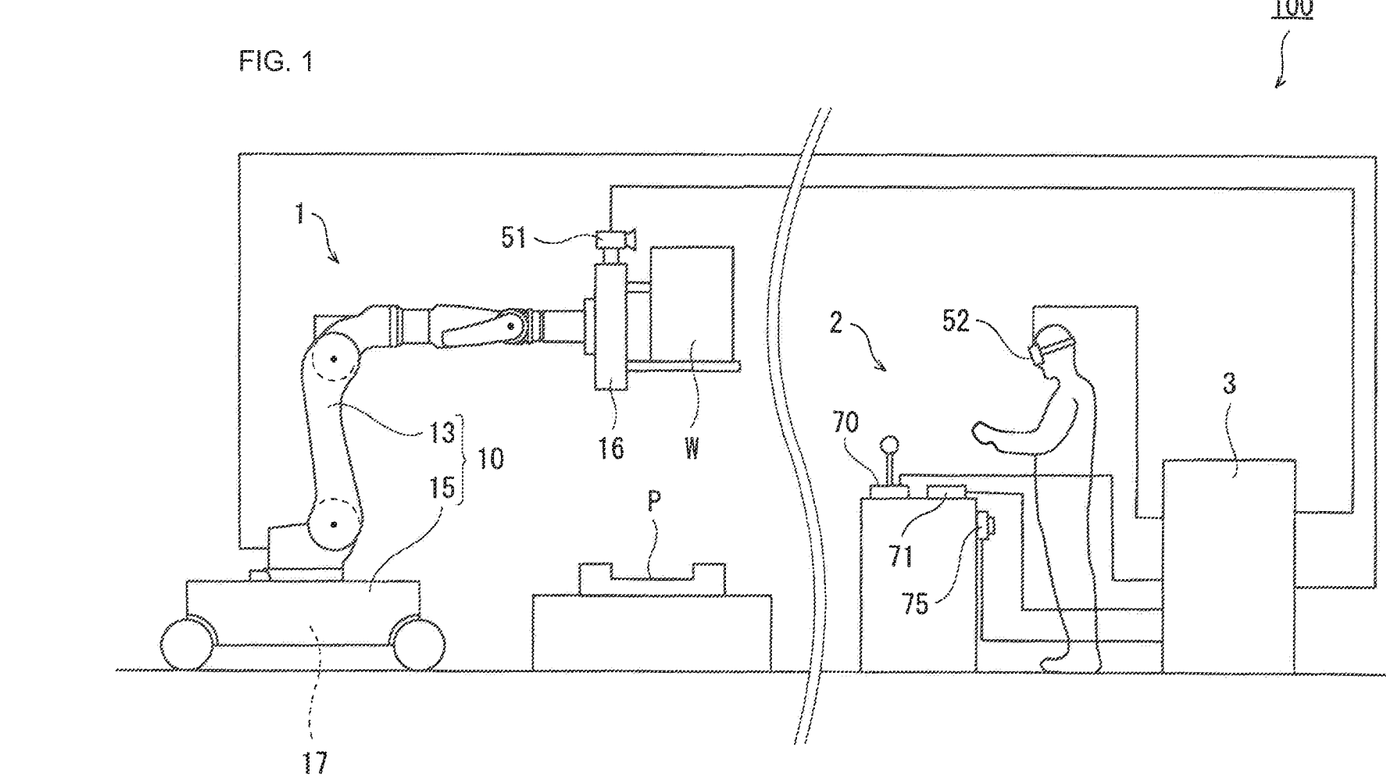
FIG. 1 is a view schematically illustrating a configuration example of a remote control robot system according to a first embodiment of the present disclosure.

FIG. 1 is a view schematically illustrating a configuration example of a remote control robot system 100 according to the first embodiment of the present disclosure.

As illustrated in FIG. 1, the remote control robot system 100 includes a robot main body 1, a remote control device 2, and a control device 3.

The remote control robot system 100 according to this embodiment is a system including a master-slave type robot in which a slave arm operates following a motion of a master arm. The remote control robot system 100 is configured so that an operator located at a position distant from a working area (outside the working area) of a slave arm 10 (a robotic arm, will be described later in detail) of the robot main body 1 can input an operational instruction to the remote control robot system 100 by moving a master arm 70 of the remote control device 2 (a robotic arm operational instruction input part, will be described later in detail), to make the slave arm 10 perform an operation corresponding to the operational instruction by a control of the control device 3 to perform a work, such as an assembling work of components. The slave arm 10 of the remote control robot system 100 is also configured so that the slave arm 10 may automatically perform a given operation by a control of the control device 3 without the operator's control of the master arm 70.

[Configuration Example of Robot Main Body]

The robot main body 1 includes the slave arm 10, an end effector 16, a traveling unit 17, and a camera 51, and is installed in the working area.

The slave arm 10 is, for example, an arm of an articulated-type industrial robot, but it is not limited to this. The slave arm 10 includes an arm main body 13 and a pedestal 15.

The arm main body 13 includes a plurality of links sequentially connected in a direction from a base-end part toward a tip-end part, and one or more joints coupling the adjacent links so that one of them is rotatable with respect to the other link. Further, the end effector 16 is coupled to the tip-end part of the arm main body 13. Moreover, the arm main body 13 is configured so that the tip-end part is moved with respect to the base-end part by rotating the joint, and the end effector 16 thus moves within a given operational area. The arm main body 13 includes a robotic arm drive part (not illustrated) which drives a plurality of joint axes. Further, the pedestal 15 supports the arm main body 13 and the end effector 16.

In this embodiment, the end effector 16 is configured to be capable of performing a holding operation for holding a workpiece and a releasing operation for releasing the held workpiece, and is attached to the tip-end part of the arm main body 13 via a wrist joint. The end effector 16 includes an end effector drive part (not illustrated) for performing the holding operation and the releasing operation. In this embodiment, the end effector 16 is configured to be capable of performing the holding operation and the releasing operation so that, for example, the assembling work of the components can be performed, but it is not limited to this. Alternatively to this, it may be configured so that, for example, a welding work and a paint work can be performed.

The traveling unit 17 is provided to the pedestal 15 and causes the entire robot main body 1 to travel. The traveling unit 17 has, for example, wheels and a wheel drive part (not illustrated) which rotatably drives the wheels. The wheel drive part rotatably drives the wheels to move the robot main body 1. Thus, in this embodiment, the robot main body 1 is a self-running robot which is self-runnable, but it is not limited to this.

The camera 51 is a camera which images operation statuses of the slave arm 10 and the end effector 16. In this embodiment, the camera 51 is attached to the tip-end part of the slave arm 10, but it is not limited to this. Alternatively to this, it may be attached to the end effector 16 or the pedestal 15. Further, it may be fixed at a given position in the working area.

[Configuration Example of Remote Control Device]

The remote control device 2 is installed outside the working area, is communicably connected to the remote control device, and controls the operation of the robot main body 1.

The remote control device 2 includes the master arm 70, a contactless action detecting part 71, a mode selecting part 75, and a monitor 52.

The master arm 70 is a device which receives an input of an operational instruction for the slave arm 10 from the operator. In this embodiment, the master arm 70 is a device by which a target attitude of the slave arm 10 can be inputted and an operation mode for the slave arm 10 can be inputted.

Figure 2:
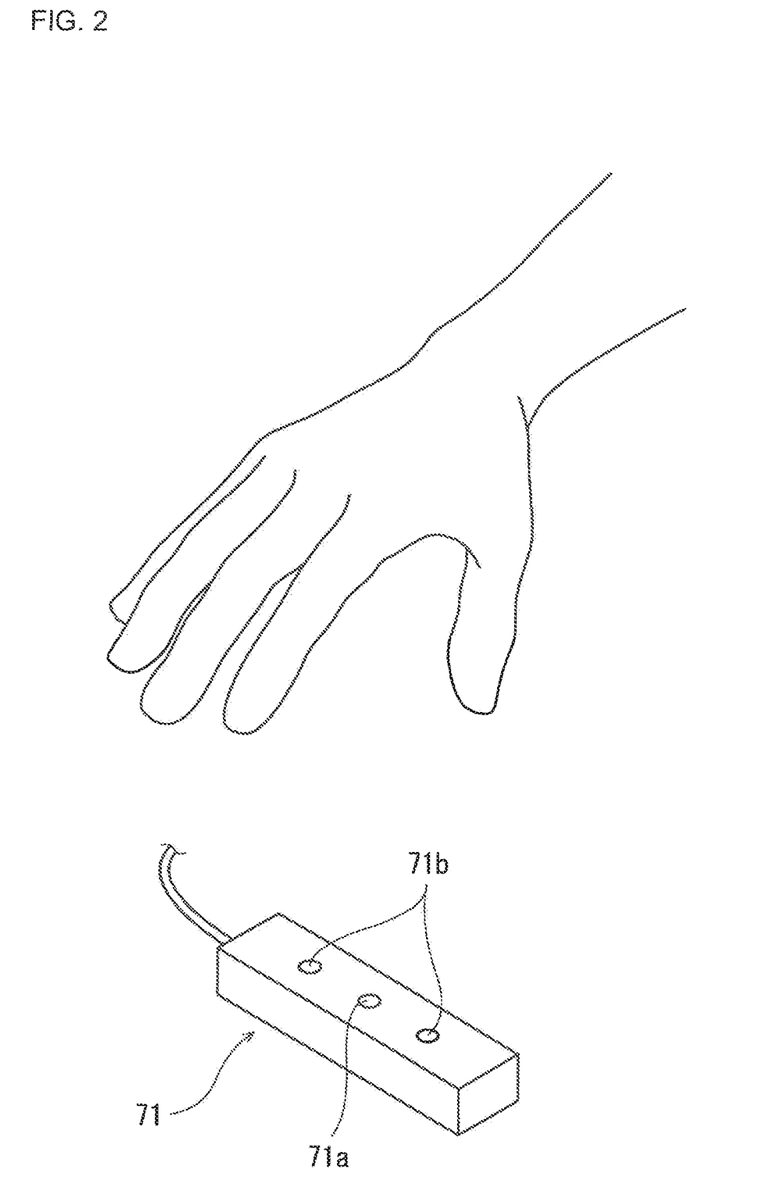
FIG. 2 is a perspective view illustrating a configuration example of a contactless action detecting part of the remote control robot system in FIG. 1.

FIG. 2 is a perspective view illustrating a configuration example of the contactless action detecting part 71.

The contactless action detecting part 71 detects, without touching, a contactless action which includes one or more given operating condition parameter change instructing actions of the operator within a given detection area. The contactless action refers to actions related to body gestures, hand gestures, and vocalizations of the operator, and does not include actions of touching an input device to control it. The contactless action includes, for example, the operator making a hand gesture, the operator speaking, the operator exhaling, the operator changing his/her posture, the operator shaking his/her neck up-and-down or to the sides, the operator tilting the neck, the operator blinking, or the operator gazing at a given place, the operator changing his/her facial expression, the operator stomping, and the operator chewing.

In this embodiment, the given operating condition parameter change instructing action is the operator making the hand gesture, and the contactless action detecting part 71 is a detector which detects the operator's hand gesture within a range set above the contactless action detecting part 71. As illustrated in FIG. 2, the contactless action detecting part 71 includes an infrared radiator 71a for radiating an infrared ray upwardly and a stereo camera 71b for receiving the infrared ray radiated from the infrared radiator 71a and reflected on a target object. It is further configured to calculate an attitude of each finger (a shape of a hand) and a motion of the hand based on an image captured by the stereo camera 71b. Further, the contactless action detecting part 71 is installed near the master arm 70 and configured to be capable of manipulating the robot main body 1 while parallelly performing an input of the operational instruction to the master arm 70 and an input of the operating condition parameter change instructing action to the contactless action detecting part 71. For example, LEAP (®) of Leap Motion Inc. may be used as the contactless action detecting part 71.

The mode selecting part 75 is an input part for the operator to input a selecting instruction of a working mode in which the slave arm 10 is operated, and it is possible to input the selecting instruction of one working mode from an automatic mode, a correctable automatic mode, and a manual mode which are described later.

The monitor 52 is a monitor for the operator to confirm a work situation of the slave arm 10. The monitor 52 is installed in a space where the master arm 70 is provided. Further, in this embodiment, the monitor 52 is, for example, a head mounted display which may be attached to the operator's head, but it is not limited to this.

[Configuration Example of Control Device]

Figure 3:
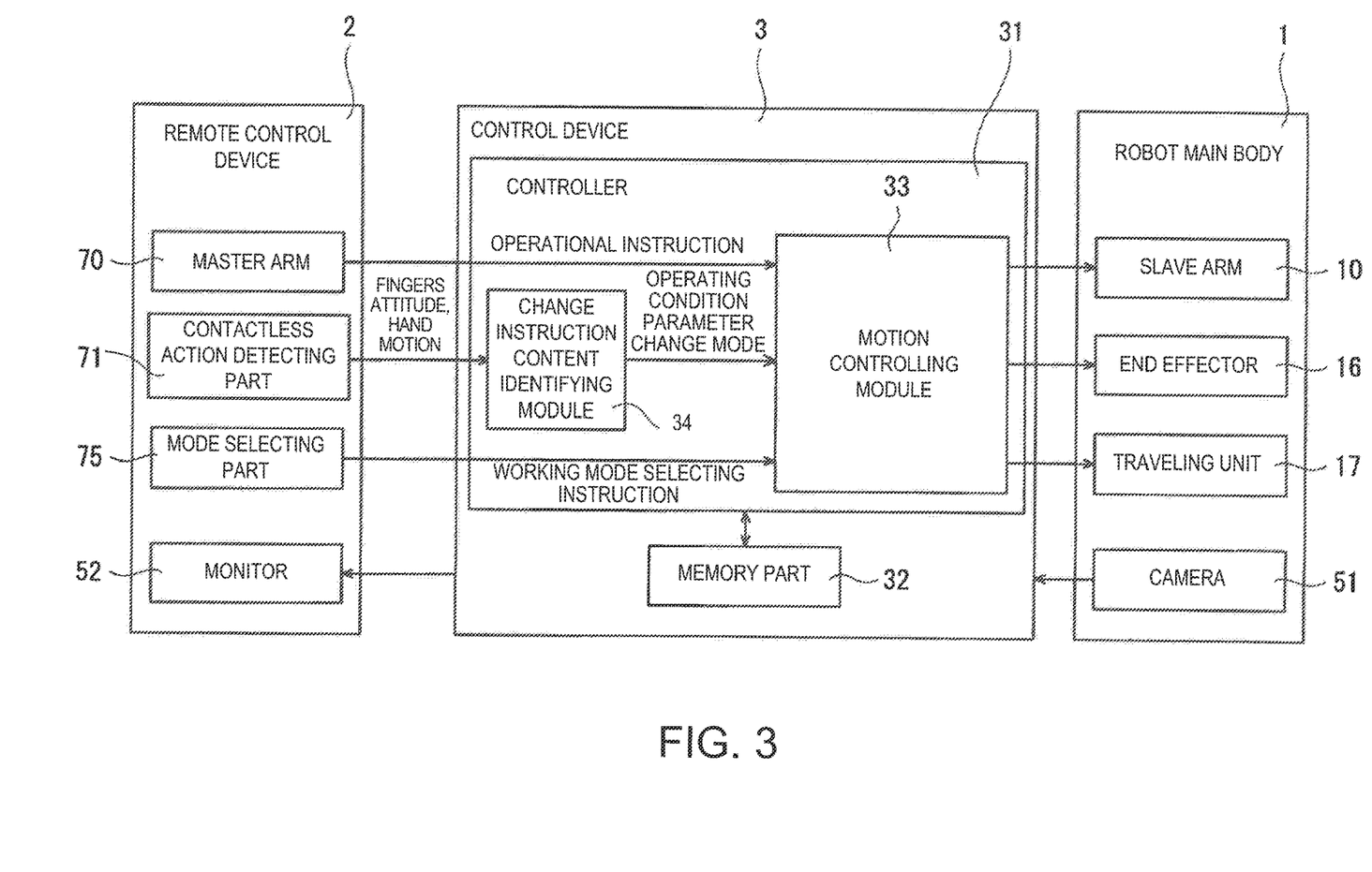
FIG. 3 is a block diagram schematically illustrating a configuration example of a control system of the remote control robot system in FIG. 1.

FIG. 3 is a block diagram schematically illustrating a configuration example of a control system of the remote control robot system 100.

The control device 3 is communicably connected to the remote control device 2 and controls the operation of the robot main body 1.

As illustrated in FIG. 3, the control device 3 includes a controller 31 and a memory part 32. The control device 3 may be comprised of a single controller which performs a central control or a plurality of controllers which perform distributed controls.

The controller 31 is, for example, comprised of a microcontroller, a CPU, an MPU, a logic circuit, a PLC, etc.

The controller 31 includes a motion controlling module 33 and a change instruction content identifying module 34. The motion controlling module 33 and the change instruction content identifying module 34 are functional blocks implemented by an arithmetic unit executing a given control program stored in the memory part 32.

The motion controlling module 33 controls the operation of the robot main body 1, including the operation of the slave arm 10, the operation of the end effector 16, and the operation of the traveling unit 17. The controls of operation of the end effector 16 and the operation of the traveling unit 17 are performed, for example, by controlling a current supplied to each drive part.

The motion controlling module 33 is configured to control the slave arm 10 according to one mode selected by the mode selecting part 75 from the manual mode, the automatic mode, and the correctable automatic mode.

The manual mode is a working mode in which the control device 3 operates the robot main body 1 according to the operational instruction inputted to the remote control robot system 100 via the master arm 70. That is, in the manual mode, the motion controlling module 33 controls the operation of the slave arm 10 based on the operational instruction inputted to the master arm 70. This manual mode includes a mode in which, when the control device 3 operates the robot main body 1 based on the operational instruction inputted by the operator controlling the master arm 70, the control device 3 applies a correction in a part of the operational instruction inputted by the operator to operate the robot main body 1.

The automatic mode is a working mode in which the control device 3 operates the robot main body 1 according to a preset operation mode stored in the memory part 32. Note that, it is configured such that in the state where the automatic mode is selected, even if the operator inputs an operational instruction by controlling the master arm 70, the control device 3 does not reflect the inputted operational instruction to the operation mode of the robot main body 1.

The correctable automatic mode is a working mode in which, when the operator inputs the operational instruction by controlling the master arm 70 in a state where the control device 3 is operating the robot main body 1 according to the preset operation mode stored in the memory part 32, the control device 3 applies a correction in a part of the preset operation mode to operate the robot main body 1.

In this embodiment, the operation of the slave arm 10 in the correctable automatic mode is controlled by correcting target angular positions of the plurality of joint axes of the preset operation mode stored in the memory part 32 based on angular positions of the corresponding joint axes received from the master arm 70, and by controlling with the motion controlling module 33 the robotic arm drive part of the arm main body 13 to bring the angular positions of the plurality of joint axes of the slave arm 10 to the respective corrected target angular positions. Thus, the slave arm 10 is configured to operate upon the correction by the motion of the master arm 70.

The change instruction content identifying module 34, based on change instruction content data stored in the memory part 32, determines one hand gesture of the operator detected by the contactless action detecting part 71, that is, an operating condition parameter change mode of the robot main body 1 corresponding to the operating condition parameter change instructing action.

In addition, the controller 31 is configured to process information of an image captured by the camera 51 and then output it to the monitor 52. Thus, the operator can control the master arm 70 while checking the work situation of the slave arm 10 displayed on the monitor 52. Note that the camera 51 and the monitor 52 may be connected directly to each other without going through the control device 3.

Figure 4:
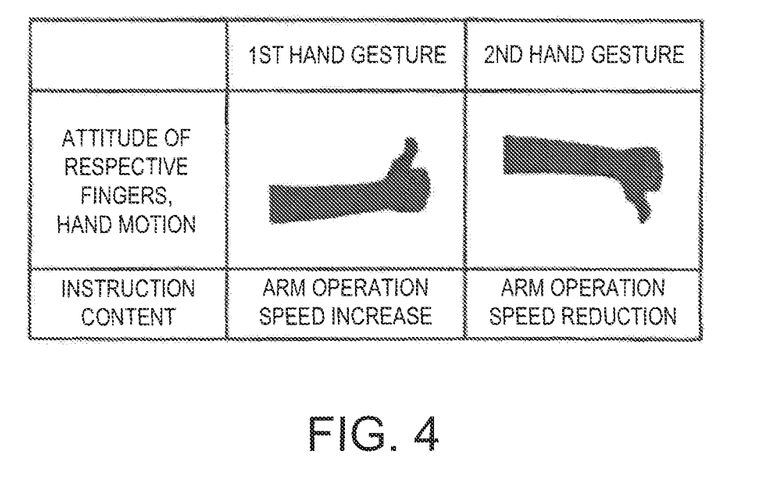
FIG. 4 is a view illustrating a configuration example of change instruction content data stored in a memory part of the remote control robot system in FIG. 1.

FIG. 4 is a view illustrating a configuration example of the change instruction content data stored in the memory part 32.

The memory part 32 has memories, such as a ROM and a RAM. The memory part 32 stores given programs and the controller 31 reads and executes these control programs to control the operation of the robot main body 1. Further, as illustrated in FIG. 4, the memory part 32 stores change instruction content data which defines the operating condition parameter change mode of the robot main body 1 corresponding to each of one or more operating condition parameter change instructing actions (hand gestures).

That is, in this embodiment, the change instruction content data includes data which defines operating condition parameter change modes related to "arm operation speed increase" and "arm operation speed reduction" which are associated with given hand gestures.

As illustrated in FIG. 4, a first hand gesture in which a thumb is extended upwardly with a hand closed is associated with the operating condition parameter change mode related to "arm operation speed increase." The operating condition parameter change mode related to "arm operation speed increase" is a mode in which the operation speed of the arm main body 13 is increased.

Further, as illustrated in FIG. 4, a second hand gesture in which a thumb is extended downwardly with the hand closed is associated with the operating condition parameter change mode related to "arm operation speed reduction." The operating condition parameter change mode related to "arm operation speed reduction" is a mode in which the operation speed of the arm main body 13 is reduced. In this embodiment, the given reference attitude is an attitude in which a workpiece W which is held by the end effector 16 is located at a position suitable for transporting the workpiece W.

The first and second hand gestures are not limited to the modes described above but hand gestures matching an operator's impression on the operating condition parameter change instruction content may be selected and set as operating condition parameter change instructing actions. Thus, a required period of time for the operator to memorize the correspondence between the operating condition parameter change instruction and the hand gesture (operating condition parameter change instructing action) and be familiar with the method of manipulating the remote control robot system 100 can be shortened.

Further, since it is possible to input the operating condition parameter change instruction to the contactless action detecting part 71 without touching, there is no need to visually recognize the contactless action detecting part 71 at the time of inputting an operating condition parameter change instruction to the contactless action detecting part 71, and it is possible to, for example, input the operating condition parameter change instruction to the contactless action detecting part 71 while keeping the focus on the monitor 52. Therefore, it is possible to promptly input the operating condition parameter change instruction, and prevent the work from being interrupted by moving his/her eyes away from the monitor 52.

Furthermore, it is possible that hand gestures which are clearly distinguishable from each other as one of the first and second hand gestures are selected as the operation instructing actions, preventing incorrect input and erroneous recognition by the operator.

Note that in this embodiment, the first or second hand gesture is all inputted by one of the operator's hands. Thus, it is possible to make a hand gesture with one hand to input the operating condition parameter change instruction for the robot main body 1 to the remote control robot system 100, while simultaneously controlling the master arm 70 with the other hand to input the operational instruction for the slave arm 10 to the remote control robot system 100.

The signals outputted from the master arm 70, the contactless action detecting part 71, and the mode selecting part 75 of the remote control device 2 are inputted to the control device 3. Further, the signal outputted from the camera 51 is inputted to the control device 3.

It is configured such that the communication between the remote control device 2 and the control device 3 and the communication between the control device 3 and the robot main body 1 are performed by a manner of using wire or wirelessly as appropriate.

Operation Example

Next, an operation example of the remote control robot system 100 will be described.

This operation example is an operation example in a case where the workpiece W stored in a workpiece storage is installed at an installation position P (see FIG. 1).

The operator controls the master arm 70 to operate the slave arm 10 to move the workpiece W, which is held by the end effector 16, toward an installation position P. Here, when the operator makes the first hand gesture which includes the hand shape by which a parameter value rises, the contactless action detecting part 71 detects the first hand gesture, and transmits the attitudes of the respective fingers and the hand motion related to the first hand gesture to the control device 3. Then, the change instruction content identifying module 34 determines that the operating condition parameter change instruction related to the change mode of "arm operation speed increase" has been inputted to the remote control robot system 100 based on the first hand gesture. Then, the motion controlling module 33 increases the operation speed of the arm main body 13 to control the operation of the arm main body 13. Thus, the workpiece W can promptly be moved close to the installation position P.

Further, when the workpiece W moves close to the installation position P and the operator makes the second hand gesture which includes the hand shape by which the value drops, the change instruction content identifying module 34 determines that the operating condition parameter change instruction related to the change mode of "arm operation speed reduction" has been inputted to the remote control robot system 100 based on the second hand gesture. Then, the motion controlling module 33 increases the operation speed of the arm main body 13 to control the operation of the arm main body 13. Thus, the workpiece W can be located at the installation position P with high precision.

As described above, in the remote control robot system 100 according to the present disclosure, the operator can select and set the action matching the impression on the operating condition parameter change instruction content as the operating condition parameter change instructing action and, by using the set operating condition parameter change instructing action, input the operating condition parameter change instruction corresponding to this operating condition parameter change instructing action, to the remote control robot system 100. Thus, a required period of time for the operator to memorize the correspondence between the operating condition parameter change instruction and the hand gesture (operating condition parameter change instructing action) and be familiar with the method of manipulating the remote control robot system 100 can be shortened.

Further, since it is possible to input the operating condition parameter change instruction to the contactless action detecting part 71 without touching, there is no need to visually recognize the contactless action detecting part 71 at the time of inputting the operating condition parameter change instruction, and it is possible to, for example, input the operating condition parameter change instruction to the contactless action detecting part 71 while keeping the focus on the monitor 52. Therefore, it is possible to promptly input the operating condition parameter change instruction, and it is possible to prevent the work from being interrupted by moving his/her eyes away from the monitor 52.

Furthermore, it is possible that actions which are clearly distinguishable from each other as the respective operating condition parameter change instructing actions are selected and set as the respective operating condition parameter change instructing actions, preventing incorrect input and erroneous recognition by the operator.

Second Embodiment

Hereinafter, configurations and operations of the second embodiment will be described focusing on differences from the first embodiment.

Figure 5:
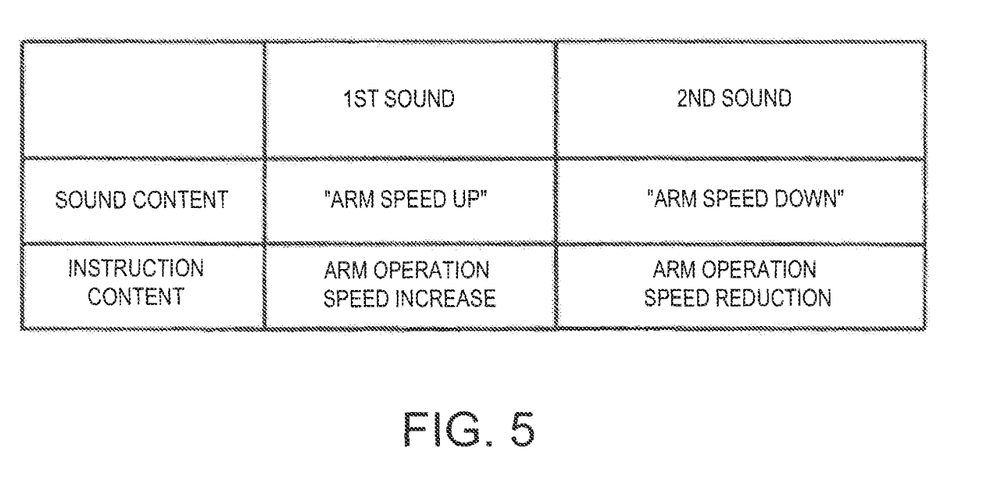
FIG. 5 is a view illustrating a configuration example of change instruction content data according to a second embodiment of the present disclosure.

FIG. 5 is a view illustrating a configuration example of change instruction content data according to this embodiment, which is stored in the memory part 32.

In the first embodiment, the operating condition parameter change instructing action is the operator's hand gesture and the contactless action detecting part 71 is the detector for detecting the operator's hand gesture. Meanwhile in this embodiment, the operating condition parameter change instructing action is operator's sound of voice, and the contactless action detecting part is a detector for detecting the sound, for example, a microphone.

Further, in the first embodiment, the change instruction content data includes the definition of operating condition parameter change modes related to "traveling speed change" and "arm operation speed change" which are associated with given hand gestures. Meanwhile in this embodiment, the change instruction content data includes the definition of the operating condition parameter change modes related to "arm operation speed increase" and "arm operation speed reduction" which are associated with given sounds.

As illustrated in FIG. 5, the operating condition parameter change mode related to "arm operation speed increase" is associated with a first sound related to a sound of voice "arm speed up." Further, the operating condition parameter change mode related to "arm operation speed reduction" is associated with a second sound related to a sound of voice "arm speed down." Note that, the change modes of the operating condition parameters related to "arm operation speed increase" and "arm operation speed reduction" are the similar as those in the above embodiment.

As described above, in this embodiment, by inputting the first and second sounds to the contactless action detecting part 71, the motion controlling module 33 operates the robot main body 1 according to the corresponding operation modes.

Third Embodiment

Figure 6:
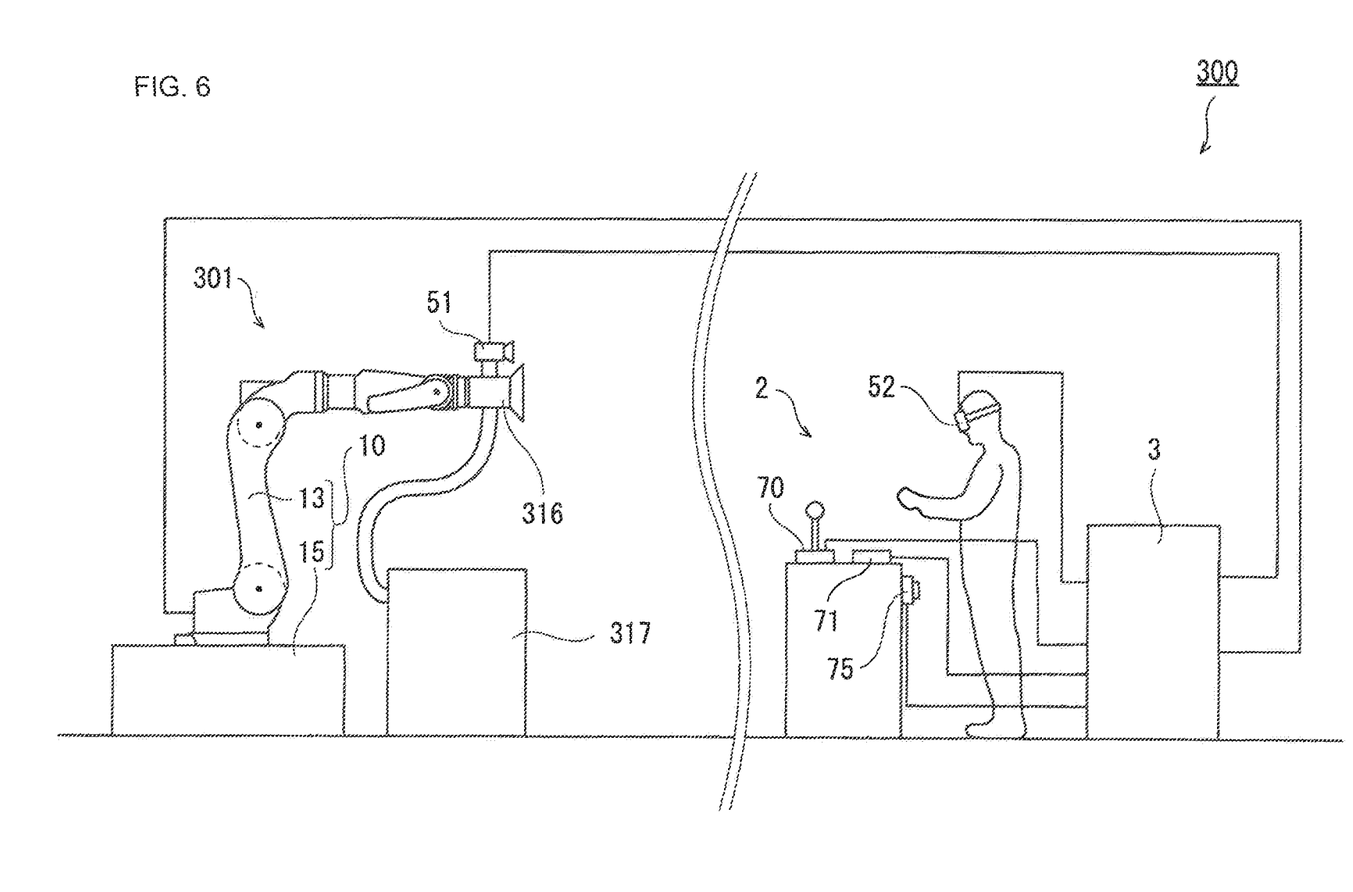
FIG. 6 is a view schematically illustrating a configuration example of a remote control robot system according to a third embodiment of the present disclosure.

FIG. 6 is a view schematically illustrating a configuration example of a remote control robot system 300 according to a first embodiment of the present disclosure.

In the first embodiment, the robot main body 1 includes the slave arm 10, the end effector 16, the traveling unit 17, and the camera 51, and the end effector 16 is configured so that, for example, the holding operation and the releasing operation can be performed to implement the assembling work of components.

In this regard, as illustrated in FIG. 6, in this embodiment, a robot main body 301 includes a slave arm 10, an end effector 316 which is a discharge gun, and a camera 51. Further, the remote control robot system 100 includes a supply device 317 for supplying paint to the discharge gun. The supply device 317 is configured to drive under a control of a motion controlling module 33.

Figure 7:
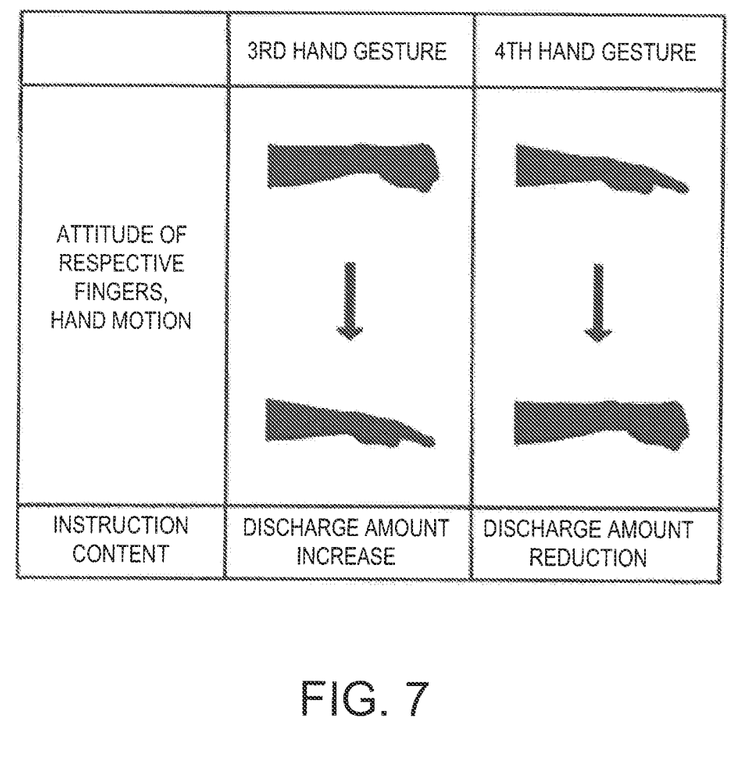
FIG. 7 is a view illustrating a configuration example of change instruction content data stored in a memory part of the remote control robot system in FIG. 6.

FIG. 7 is a view illustrating a configuration example of change instruction content data stored in a memory part 32.

As illustrated in FIG. 7, in this embodiment, the change instruction content data includes change modes of operating condition parameters related to "discharge amount increase" and "discharge amount reduction" associated with given hand gestures.

Further, the operating condition parameter change mode related to "discharge amount increase" is associated with a third hand gesture including a change, in a state where the back of the hand is facing up, from a mode in which the hand is closed (first mode) to a mode in which the hand is opened (second mode). The operating condition parameter change mode related to "discharge amount increase" is a mode in which the discharge amount of paint to be discharged from the supply device 317 is increased.

Further, the operating condition parameter change mode related to "discharge amount reduction" is associated with a hand gesture which includes an opposite change from the change mode of the hand gesture related to the discharge amount increase, that is, a fourth hand gesture including a change, in the state where the back of the hand is facing up, from the mode in which the hand is opened (second mode) to the mode in which the hand is closed (first mode). The operating condition parameter change mode related to "discharge amount reduction" is a mode in which the discharge amount of paint to be discharged from the supply device 317 is reduced.

Operation Example

Next, an operation example of the remote control robot system will be described.

This operation example is an operation example in which the robot main body 301 is operated to apply the paint to a target object.

The operator controls the master arm 70 to operate the slave arm 10 to apply the paint to the target object. Here, when the operator determines that the amount of paint discharged from the end effector 316 is small and makes the third hand gesture which includes the hand shape and motion like releasing a grip, the contactless action detecting part 71 detects the third hand gesture and transmits the attitudes of the respective fingers and the hand motion related to the third hand gesture to the control device 3. Further, the change instruction content identifying module 34 determines that the operating condition parameter change instruction related to the change mode of "discharge amount increase" has been inputted to the remote control robot system 100 based on the third hand gesture. Then, the motion controlling module 33 controls the supply device 317 to increase the amount of paint discharged from the end effector 316.

On the other hand, when the operator determines that the amount of paint discharged from the end effector 316 is small and makes the fourth hand gesture which includes the hand shape and motion like closing the grip, the change instruction content identifying module 34 determines that the operating condition parameter change instruction related to the change mode of "discharge amount reduction" has been inputted to the remote control robot system 100 based on the fourth hand gesture. Then, the motion controlling module 33 controls the supply device 317 to reduce the amount of paint discharged from the end effector 316.

Thus, the operator can suitably input the increase/reduction instruction for the value of the operating condition parameter to the remote control robot system.

Fourth Embodiment

In the first embodiment, the contactless action detecting part 71 for detecting the operator's hand gesture includes the infrared radiator 71a, and the stereo camera 71b for receiving the infrared ray radiated from the infrared radiator 71a and reflected on the target object. Meanwhile in this embodiment, the contactless action detecting part 71 for detecting the operator's hand gesture is a glove to be worn on the operator's hand, and includes a sensor for detecting the attitude of each finger and the motion of the hand.

Fifth Embodiment

In the first embodiment, the control device 3 operates the robot main body 1 in accordance with the operational instruction inputted via the contactless action detecting part 71 in the manual mode, but without limiting to this, it may be operated in the correctable automatic mode.

Modifications

In the above embodiments, the master arm 70 is a device by which the target attitude of the slave arm 10 can be inputted, but it is not limited to this. Alternatively to this, the master arm may be a device by which a target position and target attitude of the end effector 16 are inputted. Further, in the manual mode, the motion controlling module 33 may calculate the attitude of the slave arm 10 at which the end effecter takes the detected target position and target attitude, and control the operation of the slave arm 10 so that the slave arm 10 takes the attitude.

Further, the operating condition parameter related to the operating condition of the robot main body is not limited to those of the configurations illustrated in the above embodiments. Alternatively to this, it may be force, acceleration, vibration or rigidity of the robot arm.

From the above description, many improvements and other embodiments of the present disclosure are apparent for a person skilled in the art. Therefore, the above description is to be interpreted only as illustration, and it is provided in order to teach a person skilled in the art the best mode in which the present disclosure is implemented. Details of the structures and/or functions of the present disclosure may be substantially changed without departing from the spirit of the present disclosure.

DESCRIPTION OF REFERENCE CHARACTERS

1 Robot Main Body
2 Remote Control Device
3 Control Device
10 Slave Arm
13 Arm Main Body
15 Pedestal
16 End Effector
17 Traveling Unit
31 Controller
32 Memory Part
33 Motion Controlling Module
34 Change Instruction Content Identifying Module
51 Camera
52 Monitor
70 Master Arm
71 Contactless Action Detecting Part
75 Mode Selecting Part
100 Remote Control Robot System

The invention claimed is:

1. A remote control robot system, comprising:
a robot main body having a robotic arm;
a remote control device including:
    a robotic arm operational instruction input part by which an operational instruction for the robotic arm is inputted; and
    a contactless action detecting part configured to detect a contactless action including at least one given operating condition parameter change instructing action by an operator; and
a control device communicably connected to the remote control device and configured to control operation of the robot main body, the control device including:
    a memory part configured to store change instruction content data defining a change mode of an operating condition parameter related to an operating condition of the robot main body corresponding to the at least one operating condition parameter change instructing action;
    a change instruction content identifying module configured to identify the change mode of the operating condition parameter corresponding to one of the operating condition parameter change instructing action detected by the contactless action detecting part based on the change instruction content data; and
    a motion controlling module configured to control operation of the robot main body by changing the operating condition of the robot main body based on the change mode of the operating condition parameter identified by the change instruction content identifying module.

2. The remote control robot system of claim 1, wherein the at least one operating condition parameter change instructing action includes a first action including a change from a first mode to a second mode, and a second action including a change from the second mode to the first mode, and
wherein the change instruction content data includes a definition of the operating condition parameter change mode corresponding to the first action by which a value of the given operating condition parameter is increased, and a definition of the operating condition parameter change mode corresponding to the second action by which the value of the given operating condition parameter is reduced.

3. The remote control robot system of claim 1, wherein the operating condition parameter change instructing action is an operator's hand gesture.

4. The remote control robot system of claim 3, wherein the hand gesture is inputted by one of operator's hands.

5. The remote control robot system of claim 1, wherein the operating condition parameter change instructing action is operator's sound of voice.

* * * * *